United States Patent [19]
Chagny et al.

[11] 3,944,824
[45] Mar. 16, 1976

[54] METHOD AND DEVICE FOR SAMPLING GASES

[75] Inventors: Jean Chagny, Lyon; Guy Francoise, Jardin; Daniel Thevenet, Bron, all of France

[73] Assignee: Entreprise de Recherches et d'Activites Petrolieres Elf, Paris, France

[22] Filed: Sept. 17, 1974

[21] Appl. No.: 506,722

[30] Foreign Application Priority Data
Sept. 21, 1973 France ............................ 73.33933

[52] U.S. Cl. ................. 250/288; 250/281; 250/282
[51] Int. Cl.² .................................................. B01D 59/44
[58] Field of Search ................. 250/281, 282, 288; 23/232 R, 254 R

[56] References Cited
UNITED STATES PATENTS

| | | | |
|---|---|---|---|
| 2,412,359 | 12/1946 | Roper | 250/288 |
| 3,066,220 | 11/1962 | Nief et al. | 250/288 |

Primary Examiner—Archie R. Borchelt
Assistant Examiner—B. C. Anderson
Attorney, Agent, or Firm—Lane, Aitken, Dunner & Ziems

[57] ABSTRACT

In order to analyze gaseous compounds of a mixture which have a mass below a given value, a fraction containing a number of phases is continuously sampled in a loop mounted in parallel with a main circuit under conditions of pressure such that the Reynolds numbers in the main circuit and the sampling loop are equivalent. The mixture is passed through traced pipes, at least one dust remover and at least one heat exchanger in which a heat-transporting fluid is circulated at an adjustable temperature $T_1$; condensed and gaseous fractions of the mixture are collected in a flash drum placed in an enclosure at an adjustable temperature $T_2$; the products of the mixture are then passed to an analytical instrument, their mass being such that they are in gaseous form at the temperature $T_2$.

8 Claims, 1 Drawing Figure

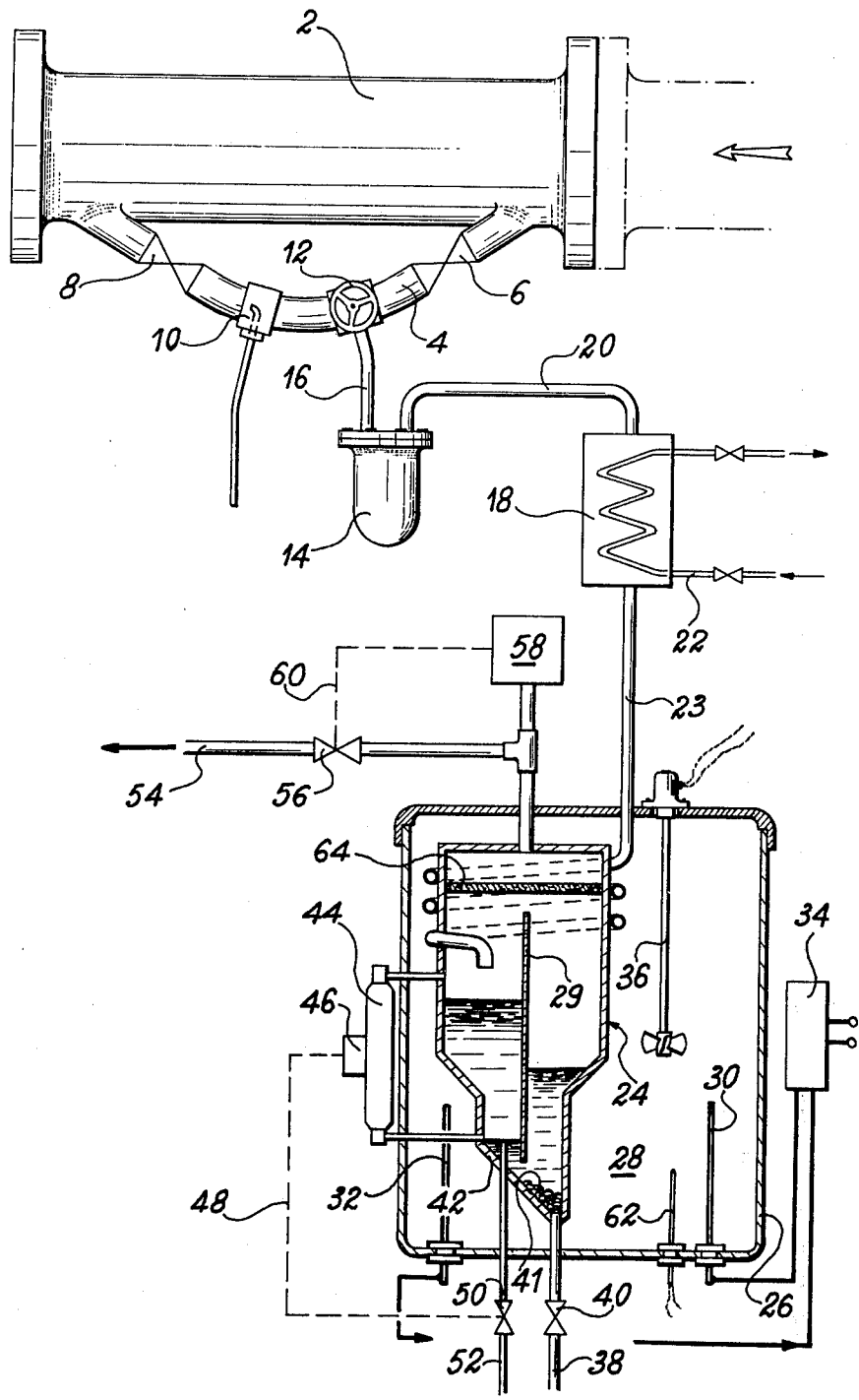

METHOD AND DEVICE FOR SAMPLING GASES

This invention relates to a method for continuously taking samples of a mixture containing a number of phases and to a device which serves to carry out said method and comprises a so-called flash drum together with the fluid-circuits which are connected thereto; said drum is employed for the purpose of taking continuously and feeding to an analytical instrument samples of the gaseous products which are present in said mixture and the molecular mass of which is below a controllable limit.

It is known that, in order to analyze the gas phase of a mixture containing a number of phases, it is useful especially in mass spectrometry to limit the number of gaseous compounds to be subjected to quantitative analysis to those whose molecular mass is lower than a maximum molecular mass, this limiting value being controlled. In fact, mass spectrometers do not withstand the introduction of liquids which destroy the filament of the spectrometer. It is therefore important to ensure that the products which are passed to the mass spectrometer after sampling do not contain any liquid. It is also necessary for the purpose of quantitative analysis to limit the range of mass to be studied in order that it may thus be possible to standardize the measurements of the quantities of products detected with respect to a total mass. A convenient method of limiting the mass of gaseous compounds which are passed to a spectrometer consists in controlling the temperature of the gas mixture which is fed into the same spectrometer. The boiling point of a substance is related monotonically to the mass of said substance or in other words the boiling point of a substance rises as the mass of said substance increases. By establishing the temperature of the mixture and passing to the measuring instrument only those gaseous products which are at this temperature, the range of masses is limited to the range corresponding to the substances which are gaseous at said temperature whilst higher molecular masses correspond to condensed substances.

To this end, the condensation products derived from continuous sampling of a gas mixture are collected in a so-called flash drum in which the temperature and the pressure are adjustable. For the purpose of reliable analysis, it is important to ensure that the conditions of temperature and pressure which exist within said flash drum are defined with precision and that the continuous operation of said drum is stable. Accurate quantitative analysis of the gaseous products derived from polyphase samples and especially those derived from the effluents of a steam cracking furnace cannot be performed with conventional flash drums, the operation of which is not sufficiently stable to ensure that the analysis accurately represents the constitution of the gas phases. Furthermore, in the case of steam cracking effluents which are mainly gaseous, the difficulties attached to the presence of fine solid particles of carbon entail the need for special precautions in regard to the supply of the flash drum with samples of products to be analyzed in a continuous operation.

Summary of the Invention

The precise aim of the present invention is to provide a method for continuously sampling a mixture containing a number of phases for the analysis of gaseous compounds of said mixture which have a mass below a given value.

The invention essentially consists in continuously sampling within a sampling loop mounted in parallel with a main flow circuit in which the mixture to be analyzed is circulated a fraction of said mixture under conditions of pressure such that the Reynolds numbers within the main circuit and the sampling loop are equivalent, in passing the mixture to be analyzed within traced pipes, in causing said mixture to pass through at least one dust remover, then at least one heat exchanger in which a heat-transporting fluid circulates at an adjustable temperature $T_1$, in collecting the condensed and gaseous fractions of the mixture in a flash drum placed within an enclosure at an adjustable temperature $T_2$ and in passing to an analytical instrument the products of the mixture whose mass is such that said products are present in gaseous form at the temperature $T_2$.

The pipes are traced or in other words are heated along their entire length; this heating process is performed by means of a cylindrical sleeve which is coaxial with the pipe and through which is passed superheated steam; this tracing process prevents the formation of condensates and any danger of clogging by depositions of these condensates at particular points of the line bottom point, constrictions and so forth).

The heat exchanger has the intended function of reducing the temperature of the mixture which circulates within the pipes and thus causing intentional condensation of the heavy components which would be liable to appear further on after the flash drum for example, in the line traced with steam which terminates in the analytical instrument. As a rule, the temperature $T_2$ of the flash drum is maintained at a higher value than the temperature $T_1$ of the heat exchanger, with the result that by increasing the temperature along the pipes in which the mixture flows from the heat exchanger, it is accordingly ensured that there is no condensate in the steam which is passed to the analytical instrument at the outlet of the flash drum. In the case of analysis of steam-cracking effluents, the dust remover essentially serves to remove the greater part of the carbon particles.

In accordance with the invention, the gas mixture which is discharged from the flash drum is passed to a mass spectrometer, the temperatures $T_1$ and $T_2$ of the first heat exchanger and of the flash drum are adjusted automatically according to the range of masses of the gaseous products to be analyzed in the mass spectrometer and the flow rates of the gaseous products downstream of the flash drum are adjusted so as to obtain an acceptable time of travel along the line.

The regulation of the temperatures $T_1$ and $T_2$ permits precise and stable operating conditions for the flash drum. Adjustment of temperatures is automatic. Moreover, the value which limits the flow rate of gas towards the analytical instrument and is disposed downstream of the flash drum is thus located at the end of the sampling apparatus in order that the pressure should be controlled as accurately as possible within the flash drum.

The invention also provides a device for carrying out the method, said device being characterized in that it comprises:

a sampling loop mounted in parallel on the main flow circuit for the mixture to be analyzed and comprising two valves located at the inlet and at the outlet of said sampling loop and a depressurizer downstream of a three-way valve for connecting the sampling loop pipe to a traced pipe when said valve is put into service;

a dust remover;

a heat exchanger having an adjustable temperature $T_1$;

a flash drum placed within an enclosure having an adjustable temperature $T_2$;

traced pipes for connecting the three-way valve to the dust remover, for connecting the dust remover to the heat exchanger, the heat exchanger to the flash drum, the flash drum to the analytical instrument;

a valve located downstream of the flash drum for regulating the pressure within the flash drum;

automatic means for controlling the temperatures $T_1$ and $T_2$ and the pressure within the flash drum in dependence on reference points;

means for circulating a heat-transporting liquid within the heat exchanger;

heating means for regulating the temperature of the enclosure in which the flash drum is placed;

means for controlling the level of the liquid derived from the condensation products within the flash drum;

means for draining the liquid condensation products and the solid particles from the flash drum.

A preferential device for carrying out the method according to the invention comprises a so-called "crustbreaker" valve; when put into service, this valve is capable of breaking the crust of coke which is deposited as a result of accumulation of solid carbon particles.

The three-way valve aforesaid allows the gaseous products to remain permanently within the secondary loop; the opening of the valve puts the third way into service, namely the diversion of part of the flow towards the dust remover and the remainder of the sampling device.

Provision is made in said sampling loop for a steam ejector which is so arranged as to facilitate the circulation of effluents within the tube by artificially creating a partial vacuum upstream of the point of injection of the steam into the loop.

The steam ejector is so designed that the Reynolds numbers should be equivalent in both tubes.

In accordance with the invention, the dust remover is constituted by a fine-mesh wire sieve.

In the particular case of analysis of steam cracking effluents, the dust remover has the function of eliminating carbon particles by causing the effluents to flow through the meshes of a wire sieve.

The invention also provides a device for the application of a controlled temperature enclosure which surrounds the flash drum, said device being characterized in that it comprises:

a tank filled with a liquid which surrounds the flash drum;

insulated resistors which are immersed in said liquid and through which an electric current of adjustable value is passed;

stirring means for ensuring uniform temperature of the liquid contained in the tank;

means for measuring the temperature of said liquid.

In a preferential alternative embodiment of the invention, the liquid contained in the tank is a silicone oil and the stirring means are impellers immersed in said silicone oil.

The silicone oil is preferable to water within the temperature-regulating enclosure of the flash drum since it has a higher boiling point and this permits temperature adjustment in respect of higher values than in the case of water without any excessive vaporization.

In accordance with the invention, the flash drum device essentially comprises:

a flash drum having a bottom wall which is inclined to the horizontal, the lowest portion of the bottom wall of the flash drum being connected to a drain pipe fitted with a valve;

a vertical pipe which penetrates into the flash drum through the bottom wall of said drum and having an open top extremity, said pipe being fitted with an automatic-control pneumatic valve in that portion of said vertical pipe which is located outside the enclosure;

a device for measuring differential pressure between two points within the flash drum located vertically one above the other;

a vertical wall dividing the space within the flash drum into two portions which communicate at the bottom of said drum;

a metallic filter in the vicinity of the top of the flash drum upstream of the gas discharge pipe.

The valve which is connected to the drain pipe can be controlled by hand since this draining-out operation is infrequent. The differential pressure measurement makes it possible to regulate the water level by producing action on the automatic draw-off valve.

The admission of fluid into the flash drum is carried out in the portion which is fitted with a level detector in order to permit condensation of the light hydrocarbons.

Brief Description of the Drawings

A better understanding of the invention will in any case be gained from the following description of one embodiment which is given by way of non-limitative example, reference being made to the single accompanying figure which shows a diagram of the sampling apparatus.

Description of the Preferred Embodiment

As has already been mentioned, the invention consists in continuously sampling a fraction of a mixture in order to carry out a quantitative analysis of said mixture by limiting the number of gaseous compounds to those whose molecular mass is lower than a given molecular mass; this upper limit of molecular mass of the gaseous constituents is established by the stable and predetermined temperature of the flash drum, the products of high molecular mass being condensed within the flash drum.

The flash coefficients, namely the matrix of coefficients which relate the measured concentrations after the flash within the measuring instrument to the concentrations of the different products before the flash, that is to say within the mixture to be subjected to analysis, are determined either by calculation or by preliminary experimentation; the calculation of these coefficients must be performed at known values of pressure and temperature of the flash. The matrix which relates the pre-flash concentrations to the post-flash concentrations is not usually a square matrix but rather a rectangular matrix since the analysis corresponding to a given peak sometimes corresponds to a number of substances of equal mass but having different chemical compositions. The correction of the flash effects which makes it possible to find the pre-flash composition again from the post-flash composition of the gas phase is made possible in spite of the intentional limitation of the mass range by the fact that a substance is characterized by peaks at different masses. For example, heptene $C_7H_{14}$ is characterized by a majority peak having mass 41 and makes contributions to the peaks 42 and 55. After experimental or theoretical determination of said flash coefficients, the composition of the total effluents can again be found from analysis of the vapor phase. In the case of analysis of the steam cracking effluents, the operation has been carried out in the presence of hydrocarbons from hydrogen to the compounds having 12 carbon atoms. In order that the analysis of the vapor phase should be representative of the total effluents, it is essential to ensure that the flash coefficients are accurate and constant and therefore to ensure that the operating conditions are stable.

In the single accompanying figure, there is shown at 2 the main pipe in which is circulated the two-phase mixture to be analyzed. In parallel with said main pipe 2, a by-pass loop 4 is fitted with an inlet valve 6 and an outlet valve 8, an ejector 10 connected to a steam pipe in which the pressure is higher than the pressure within the loop 4 and a so-called "crust-breaker" valve 12 of the manual control type which is connected to a filter 14 through a traced pipe 16, the outlet of the filter 14 being connected to the inlet of a heat exchanger 18 through a traced pipe 20. The heat exchanger 18 is fitted with a pipe 22 in which a cooling fluid is circulated at a controlled temperature. The outlet of the heat exchanger is connected through the traced pipe 23 to a tube coil which is passed around the exterior of the flash drum and then penetrates into the interior of this latter. The flash drum 24 is located inside an enclosure 26 which is provided internally with a bath 28 of silicone oil. The space within the interior of the flash drum is divided into two parts by a metallic wall 29. Fluid is admitted through the pipe 23 in the left-hand portion of the flash drum which is fitted with a level detector 44. The flash drum is also fitted with a metallic filter 64. The resistors 30 and 32 which are supplied through a temperature regulator 34 maintain the silicone oil bath at a constant temperature which is measured by means of the thermocouple 62. Stirring of the silicone bath is performed by means of the impeller 36. The pipe 38 which is fitted with the valve 40 serves to remove the very heavy periodic condensates and solid particles deposited at the bottom of the drum. The liquid compounds (liquid hydrocarbons and water) and the solid particles 41 flow along the inclined wall 42 which forms the bottom wall of the flash drum 24 towards the pipe 38. The U-tube 44 has two branches which penetrate into the interior of the flash drum and contains a device 46 for measuring the differential pressure between two points; by means of a regulator, this measurement controls the opening of the pneumatic valve 50 located in the pipe 52 for controlling the level of liquid within the flash drum. The gases located within the flash drum are discharged to the measuring instrument through a traced pipe 54 fitted with a flow-regulating valve 56, the opening of which is controlled by a pressure regulator 60, measurement of pressure being performed by the detector 58.

During operation, the level of liquid within the flash drum is set at a fixed point (reference level) located between the two tapping points of the differential pressure detector. The water level is maintained at the top end 52 of the tube. The internal enclosure of the flash drum is of stainless steel since it is in direct contact with the hydrocarbons. The space between the two enclosures is filled with silicone oil and is fitted with a number of heating resistors such as the resistors 30 and 32 which serve to regulate the temperature of the oil bath by means of a regulator of known type (not shown in the figure) which is associated with a detector for indicating the temperature of the bath 62 (calibrated thermocouple or thermometer).

In the case of analysis of steam cracking effluents, the effluents are discharged from the heat exchanger at a temperature in the vicinity of 75°C; the liquid which passes into the heat exchanger is water at 60°C. The temperature of the silicone oil bath is of the order of 95°C. The temperature of the effluents thus rises within the flash drum but not to a sufficient extent to result in re-vaporization of the water. The temperature of the bath is maintained so as to choose a given "final point" of the gas phase, that is to say a maximum molecular mass in the case of the compounds to be analyzed in the measuring instrument. This point is determined as a function of requirements downstream, that is to say the products whose concentrations are to be measured in the mass spectrometer. The departure of the gas phase towards the mass spectrometer takes place via the line 54 which is traced with steam at 8 bars (175°C). It is thus certain that no condensates reach the mass spectrometer at this temperature, which would have a harmful effect on its operation.

Taking into account the conditions of temperature, pressure and flow rate which are imposed with precision within the flash drum, a transfer matrix can accordingly be determined experimentally. By multiplication with the composition vector of the vapor phase whose components are measured as a result of the analysis, said matrix makes it possible to determine the composition vector upstream of the flash.

What we claim is:

1. A method for continuous sampling of a mixture of a multiphase fluid for the analysis of gaseous compounds of said mixture which have a mass below a given value, comprising the steps of continuously withdrawing a portion of said mixture from a main flow circuit for said mixture, to a sampling circuit under conditions of pressure such that the Reynolds numbers within the main circuit and the sampling circuit are equivalent, removing the dust from said mixture portion, passing said mixture portion in a heat exchange relation with a heat exchange fluid at a predetermined temperature, collecting the condensed and gaseous fractions of the mixture portion in a flash drum at a predetermined temperature and passing to an analytical instrument the products of said mixture portion whose mass is such that said products are present in gaseous form at said latter predetermined temperature.

2. A method according to claim 1 wherein the gaseous products of said mixture portion discharged from the flash drum are passed to a mass spectrometer wherein said two predetermined temperatures are adjusted automatically according to the range of masses of the gaseous products to be analyzed in said mass spectrometer, and wherein the flow rate of said gaseous products is adjusted so as to obtain an acceptable time of travel to said spectrometer.

3. An apparatus for continuously sampling a mixture of a multiphase fluid for the analysis of gaseous compounds of said mixture which have a mass below a given value, comprising a sampling loop mounted in parallel with the main flow circuit for the mixture to be analyzed and comprising two valves located at the inlet and at the outlet of said sampling loop and a depressurizer downstream of a three-way valve for connecting the sampling loop to a traced pipe when said valve is put into service; a dust remover; a heat exchanger having an adjustable temperature $T_1$; a flash drum placed within an enclosure having an adjustable temperature $T_2$; traced pipes for connecting the three-way valve to the dust remover, for connecting the dust remover to the heat exchanger, the heat exchanger to the flash drum, the flash drum to the analytical instrument; a valve located downstream of the flash drum for regulating the pressure within said drum; automatic means for controlling the temperatures $T_1$ and $T_2$ and the gas flow rate downstream of the flash drum in dependence on reference points; means for circulating a heat-transporting liquid within the heat exchanger; heating means for regulating the temperature of the enclosure in which the flash drum is placed; means for controlling the level of the liquid derived from the condensation products within the flash drum; and means for draining the liquid condensation products and the solid particles from the flash drum.

4. An apparatus according to claim 3, wherein the three-way valve is adapted to break the crust of coke which is deposited as a result of accumulation of solid carbon particles.

5. An apparatus according to claim 3 wherein the dust remover is constituted by a fine-mesh wire sieve.

6. A device according to claim 3 further comprising a tank filled with a liquid which surrounds the flash drum; insulated resistors immersed in said liquid and through which an electric current of adjustable value is passed; stirring means for ensuring uniform temperature of the liquid contained in the tank; and means for measuring the temperature of said liquid.

7. A device according to claim 6, wherein the liquid contained in the tank is a silicone oil and wherein the stirring means consist of impellers immersed in said silicone oil.

8. A device according to claim 3 wherein said flash drum has a bottom wall which is inclined to the horizontal, the lowest portion of the bottom wall of the flash drum being connected to a drain pipe fitted with a valve and further comprising a vertical pipe which penetrates into the flash drum through the bottom wall of said drum and having an open top extremity, said pipe being treated with an automatic-control pneumatic valve in that portion of said vertical pipe which is located outside the enclosure; a device for measuring differential pressure at two points of the flash drum which are located vertically one above the other; a vertical wall dividing the space within the flash drum into two portions which commumicate at the bottom of said drum; and a metallic filter in the vicinity of the top of the flash drum upstream of the gas discharge pipe.

* * * * *